(12) United States Patent  
Sarvazyan

(10) Patent No.: US 7,291,109 B1  
(45) Date of Patent: Nov. 6, 2007

(54) INFANT HYDRATION MONITOR

(76) Inventor: Armen P. Sarvazyan, 1753 Linvale Harbourton Rd., Lambertville, NJ (US) 08530-3302

( * ) Notice: Subject to any disclaimer, the term of this patent is extended or adjusted under 35 U.S.C. 154(b) by 116 days.

(21) Appl. No.: 11/410,178

(22) Filed: Apr. 24, 2006

Related U.S. Application Data

(63) Continuation-in-part of application No. 10/979,940, filed on Oct. 25, 2004, now Pat. No. 7,033,321.

(51) Int. Cl.  
*A61B 8/00* (2006.01)

(52) U.S. Cl. ...................... 600/438; 600/449

(58) Field of Classification Search ........ 600/437–438, 600/442, 449, 306–307, 309, 345, 366; 73/32 R, 73/32 A, 53.01, 54.01, 61.71, 61.79, 597  
See application file for complete search history.

(56) References Cited

U.S. PATENT DOCUMENTS

| | | | |
|---|---|---|---|
| 4,008,712 A | 2/1977 | Nyboer | |
| 4,383,533 A | 5/1983 | Lovelace et al. | |
| 4,635,198 A * | 1/1987 | Hohlweck et al. | 600/448 |
| 4,926,870 A * | 5/1990 | Brandenburger | 600/437 |
| 4,976,267 A * | 12/1990 | Jeffcott et al. | 600/437 |
| 5,564,423 A * | 10/1996 | Mele et al. | 600/438 |
| 5,603,325 A * | 2/1997 | Mazess et al. | 600/442 |
| 5,606,971 A * | 3/1997 | Sarvazyan | 600/438 |
| 5,615,689 A | 4/1997 | Kotler | |
| 5,720,290 A * | 2/1998 | Buhler et al. | 600/449 |
| 5,882,303 A * | 3/1999 | Stussi | 600/407 |
| 5,973,494 A | 10/1999 | Masreliez | |
| 6,125,297 A | 9/2000 | Siconolfi | |
| 6,135,964 A * | 10/2000 | Barry et al. | 600/449 |
| 6,221,019 B1 * | 4/2001 | Kantorovich | 600/449 |
| 6,279,248 B1 | 8/2001 | Walters | |
| 6,280,396 B1 | 8/2001 | Clark | |
| 6,358,208 B1 * | 3/2002 | Lang et al. | 600/438 |
| 6,459,930 B1 | 10/2002 | Takehara | |
| 6,468,215 B1 * | 10/2002 | Sarvazyan et al. | 600/438 |
| 6,517,487 B1 * | 2/2003 | Mazess et al. | 600/449 |
| 6,585,649 B1 * | 7/2003 | Mendlein et al. | 600/438 |
| 6,687,646 B2 | 2/2004 | Mewissen | |
| 6,761,697 B2 * | 7/2004 | Rubinstenn et al. | 600/587 |
| 6,949,071 B1 * | 9/2005 | Saied et al. | 600/445 |
| 7,047,058 B1 * | 5/2006 | Dvorsky et al. | 600/407 |
| 2002/0103435 A1 * | 8/2002 | Mault | 600/439 |

* cited by examiner

*Primary Examiner*—Francis J. Jaworski

(57) ABSTRACT

An infant hydration monitor includes a hand-held probe equipped with a pair of arms extending from a housing and incorporating a broadband ultrasonic transmitter and receiver. The arms include finger openings allowing the user to adjust the distance between the transducers by manipulating the probe using fingers placed in these openings. Each transducer is mounted on a force meter so that the skin contact pressure is monitored and optionally communicated to the user using a two-color LED. Sliding distance measuring means similar to the digital caliper are incorporated into the housing to allow the probe to generate a signal indicating the distance between the transducers. A display unit optionally worn on a wrist is attached to the probe and is adapted to calculate the hydration status of an infant.

3 Claims, 4 Drawing Sheets

INFANT HYDRATION MONITOR

CROSS-REFERENCE DATA

This is a continuation-in-part of the U.S. patent application Ser. No. 10/979,940, now U.S. Pat. No. 7,033,321 filed Oct. 25, 2004 by the same inventor entitled "ULTRASONIC WATER CONTENT MONITOR AND METHODS FOR MONITORING TISSUE HYDRATION", which is incorporated herein by reference in its entirety.

BACKGROUND OF THE INVENTION

The present invention relates generally to ultrasonic measurements of biological tissue parameters for medical diagnostics, and more particularly to a method and a device for measurements of ultrasound velocity in tissue aimed at determination of hydration in infants.

Dehydration remains a leading cause of infant morbidity and mortality worldwide. In the United States, dehydration accounts for at least 10% of hospital admissions. Today, physical examination remains the most used bedside tool to detect dehydration and yet, its sensitivity remains suboptimal. Laboratory tests such as BUN (blood urea nitrogen) and bicarbonate levels require blood draws, and have been reported to be non-diagnostic unless they are extremely abnormal. The combination of history, exam and laboratory tests appears to have the best diagnostic value when assessing the hydration status of a child. However, examiners vary significantly in their agreement. Therefore, the non-invasive, objective bedside assessment of a sick infant's hydration status remains a challenge.

Physical signs of moderate to severe dehydration in children represent a significant 6 to 10% water loss. In infants less than 10 kg, the same signs represent an even more dangerous water loss of 10 to 15%. Hence, young children under 5 years old have higher risk for morbidity due to dehydration and require earlier medical response.

The clinical state of dehydration disrupts life sustaining processes at the organic and cellular level. Its clinical manifestations indicate total body water depletion leading to poor intravascular volume. The body system protectively shunts blood towards the most vital organs (heart, kidney and brain) and away from peripheral organs such as the intestines, muscles and skin. Hence, the earliest sign of dehydration may be seen in the skin and muscle tissues. If allowed to persist, the eventual result is tissue hypo-perfusion and inadequate oxygen delivery to end organs. A reduced extracellular fluid volume leads to cellular dehydration, oxygen debt and lactic acid production, which promotes further deterioration. In addition, electrolyte imbalances disrupt cellular energy metabolism and transport. The terminal phase is hypovolemic shock, multi-organ failure and death.

Sick infants have a delicate fluid and electrolyte balance that can rapidly deteriorate or be worsened iatrogenically if the water balance is not monitored closely. A non-invasive device and method of quantifying hydration in infants would be useful in the following clinical scenarios:

(a) In situations of excessive fluid loss or poor fluid intake, knowing organ tissue water contents can guide fluid resuscitation efforts. Currently, tools for assessing fluid balance are the physical examination, urine output and strict intake/output logs. Unfortunately, even the most indicative findings of poor hydration such as increased capillary refill time, abnormal skin turgor, and abnormal respiratory pattern have only modest sensitivity. Despite better performance when using classification tables that combine the diagnostic value of two or more signs, there remains the significant problem of inconsistent inter-examiner agreement. Infant hydration monitor offers an opportunity to obtain reproducible quantitative measures of tissue water content that potentially can complement traditional qualitative methods of assessing a patient's hydration status;

(b) Neonates, especially premature ones, have a very high insensible water loss to the environment (80-100 cc/kg/d) due to a poorly keratinized skin layer and a large surface area to volume ratio. Too much fluid can be loss easily leading to dehydration. Less than expected loss can mean extra fluid that contributes to lung edema in premature infants with respiratory distress syndrome. Currently in the neonatal intensive care unit (NICU), day-to-day estimates of total body water content and fluid management for each patient relies mainly on analyzing weight trends. Total body water content in neonates comprises 75-90% (premature infants having the highest portion) of the body weight, suggesting that weight changes may still be a fairly good indicator of water content shifts over time. Losing or gaining 100 gm generally correlates with a 10% shift for 1 kg premature infant. Using weight can be problematic in neonates who are too unstable to be moved onto a scale. Built-in bed scales tend to overestimate weights. Furthermore, organ growth is expected to contribute approximately 10-15 gm/kg daily depending on the balance between nutritional intake and energy expenses. It is natural to expect that changes in local tissue hydration reflect total body water content (TBWC) in neonates;

(c) For sick neonates, monitoring local tissue hydration may have value in quantifying capillary leak syndrome—a physiologic state in which increased capillary permeability lead to general edema, low intravascular volume, and organic mal-perfusion. Neonatal capillaries are more vulnerable to physiologic insults. Some authors suggested that higher levels of vascular endothelial growth factor in neonates may lead to a higher incident of capillary leak syndrome after cardiopulmonary bypass. Sick neonates developing capillary leak syndrome often have a spike gain in weight. As fluid and solutes 'leak' into the interstitial space, a vicious cycle ensues that require more fluid administration in order to maintain adequate intravascular volume and organ perfusion. Hence especially in sick neonates, monitoring local tissue hydration with a hydration monitor in conjunction with other physiological data such as blood pressure and laboratory studies may help track and quantify the interstitial movement of fluid in critically ill patients with capillary leak syndrome;

(d) Cardiac failure and venous thrombosis are clinical conditions that increase intravascular hydrostatic pressure and cause peripheral edema. Quantifying the edema can help determine the severity of disease. Currently, the physical examination offers the best non-invasive, 'simple to use' qualitative method—using a four grade scale measuring the depth of indentation made by finger pressure over a bony prominence. Unfortunately, the exam has suboptimal sensitivity and becomes apparent late in the clinical pathophysiological course. Other methods using computer tomography, magnetic resonance, and musculoskeletal ultrasonography to characterize edema rely on expert radiologists with special training and equipment not available at the bedside. Infant hydration monitor is a portable device and its ability to detect small changes in tissue water content (as little as 2%) may discover peripheral edema earlier than physical exam, perhaps triggering earlier intervention. Infant hydration monitor may clarify information gained thru current methods of estimating intravascular blood volume (i.e. echocardiogram or central venous pressure catheter, CVP). For instance, poor intravascular volume may 'yield' a normal CVP if there is right sided heart failure. The latter condition would increase venous hydrostatic pressure and lead to increase peripheral edema at the lower legs, detectable by infant hydration monitor;

(e) Unilateral limb edema is an important physical sign of venous thrombosis (VT) that requires rapid response and treatment. Its serious complications include renal insufficiency, pulmonary embolism, and stroke. In the neonatal population, indwelling catheters in the inferior vena cava can cause venous thromboses and it is standard practice to exam the associated limb daily for edema. Infant hydration monitor offers a quantitative measure of edema that may be more sensitive than the physical exam, enabling earlier detection of VT.

There are several methods for assessing total body water, as the most prominent indicator of hydration status. Most of these methods are based on bioelectrical impedance and conductance methods. U.S. Pat. No. 4,008,712 issued to Nyboer discloses method and apparatus for performing electrical measurement of body electrical impedances to determine changes in total body water in normal and deranged states of the body, U.S. Pat. No. 5,615,689 issued to Kotler discloses a method of predicting body cell mass using impedance analysis, U.S. Pat. No. 6,280,396 issued to Clark discloses an apparatus and method for measuring subject's total body water content by measuring the impedance of the body, and U.S. Pat. No. 6,459,930 issued to Takehara et al. discloses a dehydration condition judging apparatus by measuring bioelectric impedance.

The aqueous tissues of the body, due to their dissolved electrolytes, are the major conductors of an electrical current, whereas body fat and bone have relatively poor conductance properties. Significant technical problems eliminated the viability of many electrical methods for in vivo body composition analyses. Oversimplifications in formulae in the standard biological impedance analysis methods lead to problems.

There is also known a more complex approach, based on measuring resistance and reactance over a wide range of frequencies. The technique based on this approach is called bioelectrical impedance spectroscopy. U.S. Pat. No. 6,125,297 issued to Siconolfi discloses a method and apparatus for determining volumes of body fluids in a subject using bioelectrical response spectroscopy.

Regardless of the choice of single or multifrequency method, the impedance index alone is not an accurate predictor. Additional anthropometric terms (i.e., weight, age, gender, race, shoulder width, girth, waist-to-hip ratio, body mass index) need to be included in the prediction model to reduce the standard error of the estimate. In summary, the downside of the water content assessment methods based on the measurements of electrical properties of tissues is low accuracy, significant dependence of testing results on the anthropometrical features of the subject and on electrolyte balance.

None of the known prior art devices are easily adaptable for use with neonates and infants. To assess the hydration status of an infant, most practitioners rely simply on the bedside physical examination. The patient's daily weights and fluid in/fluid out are recorded. Limitations of this approach include: (1) the mentioned measures do no reflect the real hydration status in tissues directly; (2) critical patients can not be moved onto a scale and (3) bed scales have difficulty calibrating due to the equipment on the bed and using them still requires the baby to be lifted off the bed for zeroing procedures.

Since trans-epidermal water loss is a major cause of water loss in premature infants during the first week after birth, devices called evaporimeters have been developed to measure the evaporative water loss in infants. The evaporimeters reflect permeability of the stratum corneum and the infant's immature skin barrier function, but do not allow judgment regarding water deficit in the tissues or the whole organism.

Advanced laboratory techniques for assessment of body composition are potentially applicable in infants, including $D_2O$ dilution, bioelectrical impedance spectroscopy (BLA/BIS), total body electrical conductivity (TOBEC), total body potassium (TBK), and dual x-ray absorption (DXA) that can estimate total body water, total body potassium, fat-free body mass and fat content. Physicians in the neonatal intensive care unit have used BIS to guide fluid administration in newborns during the postpartum period. However for premature infants, these techniques are impractical for frequent monitoring of hydration status because they: need blood or urine samples, involve labor consuming analysis, use large equipment, have low precision (BIS), require patient transportation, and are not specific to tissue hydration.

There is therefore a need for a simple and highly accurate method and device for monitoring infant tissue hydration status.

SUMMARY OF THE INVENTION

Accordingly, it is an object of the present invention to provide an infant hydration monitor that objectively quantifies soft tissue hydration at the child's bedside.

It is another object of the present invention to overcome the drawbacks of the prior art by providing a novel method and device for monitoring infant tissue hydration by using a measurement of ultrasound velocity through soft tissue.

It is a final object of the invention to provide a lightweight, hand-held device adapted for quick determination of infant hydration status.

To design a proper hydration monitor for infant application, it is necessary to take into account numerous factors. Much smaller size of the extremities in infants and neonates compared to adults will require a significant increase in measurement accuracy. Furthermore, there is an essential need to provide much gentler attachment of ultrasonic probes to the body, taking into account much lower allowable contact pressure, sterility conditions and tenderness of the skin.

The invention is based on the experimental fact that ultrasound velocity through soft tissue is a linear function of the tissue water content. The present invention therefore encompasses methods of detecting muscle hydration and water content with high accuracy, exploiting linear nature of dependence of ultrasound propagation velocity on muscle molecular composition, affected dominantly by the content of water, which is the major molecular component of soft biological tissues.

The invention encompasses methods of detecting muscle hydration and water content by directly testing a selected muscle or group of muscles of an infant at a certain anatomical location. In a preferred embodiment, the device examines the soleus muscle (a large and accessible muscle in the human calf), where changes in water content can be easily detected.

The invention also encompasses a device for detecting muscle hydration and water content comprising a compact probe with miniature sensors adapted for easy use by physicians as it contains distance adjusting means and shaped to fit a human hand. The infant hydration monitor of the invention comprises a hand-held probe connected to a wrist-mounted electronic unit having a display. The probe has two arms with the ends extending from the probe housing. The ends are equipped with two ultrasonic broadband transducers: one transmitter and one receiver. The arms are made to slide such that the distance between the ends is adjustable and measurable. Therefore both components needed to calculate the velocity of ultrasound in tissue can be determined: time-of-flight as measured by transducers as well as the distance between the transducers as measured by the distance measuring means. The level of tissue hydration is then calculated and displayed on the display of the electronic unit. Convenient means to adjust the distance between the transducers are provided, such as finger openings in each arm. One of the transducers is mounted on a force meter so that the skin contacting force is also determined to make sure it fits in a predetermined range.

Optional embodiments provide for an additional means and procedure of measuring the temperature of tested muscle. A further specific embodiment provides for additional steps of measurement of ultrasound velocity at different sites of the body.

BRIEF DESCRIPTION OF THE DRAWINGS

A more complete appreciation of the subject matter of the present invention and the various advantages thereof can be realized by reference to the following detailed description and drawings a brief description of which is followed.

DETAILED DESCRIPTION OF THE MOST PREFERRED EMBODIMENTS OF THE INVENTION

Figure 1:
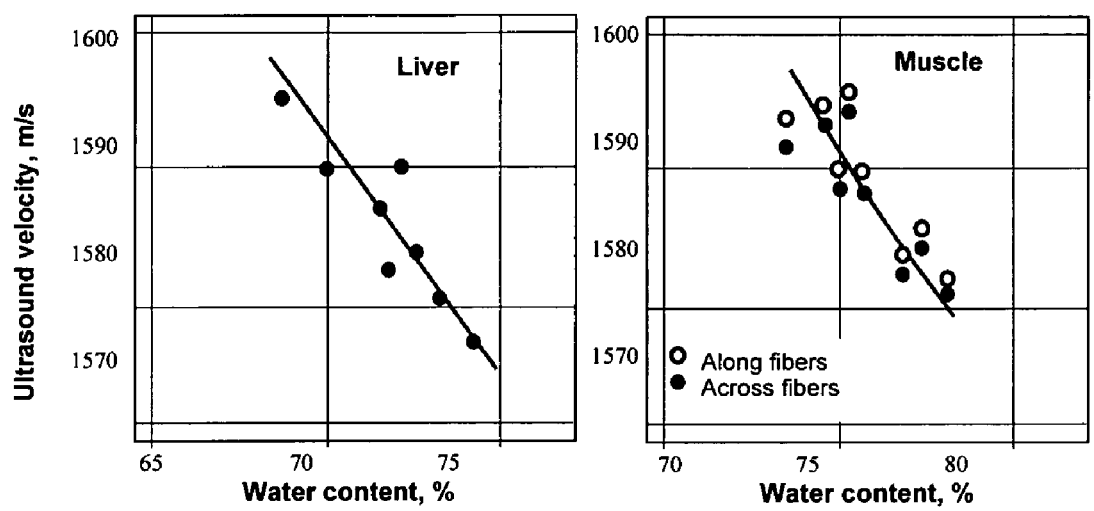
FIG. 1—Ultrasound velocity chart as a function of water content in animal liver and muscle.

The dehydration assessment according to present invention is based on measurement of ultrasound velocity in tissue, which is defined by the molecular composition of tissue and to a good approximation, is a linear function of the water content. In several publications [Gorelov S E, Lyrchikov A G, Sarvazyan A P. *Ultrasound velocity in mammalian liver as a function of water content in tissue*. Acoustical Journal, 1981, 33, N. 2, 358-360; Sarvazyan A P, Lyrchikov A G, Gorelov S E. *Dependence of ultrasonic velocity in rabbit liver on water content and structure of the tissue*. Ultrasonics. 1987 July; 25(4):244-247] incorporated herein by reference it was shown that the ultrasound velocity in soft biological tissues changes as a rate of about 3-4 m/s per 1% change of water content. It is also generally known that an easily achievable accuracy of general ultrasound velocity measurements is about 1 m/s. This suggests that a highly accurate detection of less than 1% of water content is possible by detecting a change in ultrasonic wave propagation.

Further physical foundation for this invention is given in the comprehensive review paper on mechanical and ultrasonic properties of soft tissues [Sarvazyan A. P. *Elastic properties of soft tissues*.—In: Handbook of Elastic Properties of Solids, Liquids and Gases, Volume III, Chapter 5, eds. Levy, Bass and Stern, Academic Press, 2001, 107-127.] It is shown that ultrasonic and mechanical parameters of soft tissues could be divided into two groups: one comprising parameters determined mainly by the molecular composition of tissues and the second comprising parameters that are more related to the features of higher structural levels. These two groups can be distinguished by comparing physical properties of intact tissue with those for homogenized tissue. Mechanical homogenization of tissue generally does not lead to substantial, immediate change in biochemical composition of tissue and has no significant effect on parameters determined by short-range inter- and intra-molecular interactions. For example, density and the bulk compression modulus K, which are mainly determined by the additive contributions of partial volumes of molecules composing the tissue, are not affected significantly by tissue disintegration. Transforming a tissue that has certain structure and rigidity into a structureless fluid obviously results in a dramatic change in the shear elasticity modulus G. At the same time, changes in the ultrasound velocity, which is a function of the density and bulk compression modulus K, after tissue homogenization is only about 1%. Hence, the ultrasound velocity is determined mainly by the molecular content of the tissue, and by short-range inter- and intra-molecular interactions. Consequently, from the point of view of ultrasound propagation parameters, soft tissues can be adequately modeled by a structureless fluid where only short-range inter-molecular interaction matters.

Molecular composition of tissues varies much less than their structure. Most soft tissues contain about 70-80% water. The remaining 20-30% of the tissue consists of major molecular components such as proteins and various organic and inorganic compounds of low molecular weight. These compounds are basically the same in different tissues and are often found in similar concentrations regardless of the tissue origin. In contrast, the range of variability of structural features among different tissues, such as geometrical parameters of cells and the degree of tissue mechanical heterogeneity and anisotropy are incomparably greater.

The ultrasound velocity (or the bulk elasticity modulus) is constant for most of the soft tissues within less than ±5%. Meanwhile, the structure-sensitive shear elasticity modulus for different soft tissues varies over four orders of magnitude and even within one tissue may change by hundreds of percent during such processes as an ordinary muscle contraction.

Ultrasound propagation parameters were measured in a variety of biological tissues, particularly in samples from beef and pork undercuts, with respect to composition and structure. It was demonstrated that tissue biochemical (molecular) composition principally determines the velocity, while the structural and intracellular interactions are of less influence. If protein/fat ratio is a constant for the certain specimen, changes of the water content in intact or homogenized states is the main determinant of the velocity. FIG. 1 shows experimental results extracted from the publications [Gorelov S E, Lyrchikov A G, Sarvazyan A P. *Ultrasound velocity in mammalian liver as a function of water content in tissue*. Acoustical Journal, 1981, 33, N. 2, 358-360; Sarvazyan A P, Lyrchikov A G, Gorelov S E. *Dependence of ultrasonic velocity in rabbit liver on water content and structure of the tissue*. Ultrasonics. 1987 July; 25(4):244-247] for ex vivo animal tissues in intact condition at 25° C. The experimental data obtained on rabbit liver and beef skeletal muscle along and across fibers are given. The water content in the tissue samples was determined by dry to a constant mass at 110° C. with relative measurement accuracy of 0.5%. In liver tissue, the slope of the velocity graph versus the water content is about 3.5 m/s for 1% of water content. In muscle tissue, the water content varied in different samples from 73% to 78% and caused an averaged variation of the velocity of about 17 m/s, that is 3.4 m/s per 1% of muscle water content. These results form the basis for an approximate quantitative estimation that 1% change in muscle water content in human muscle at body temperature may cause a velocity shift of about 3 m/s (higher temperature leading to a lower slope of velocity vs. muscle water content).

Figure 2:
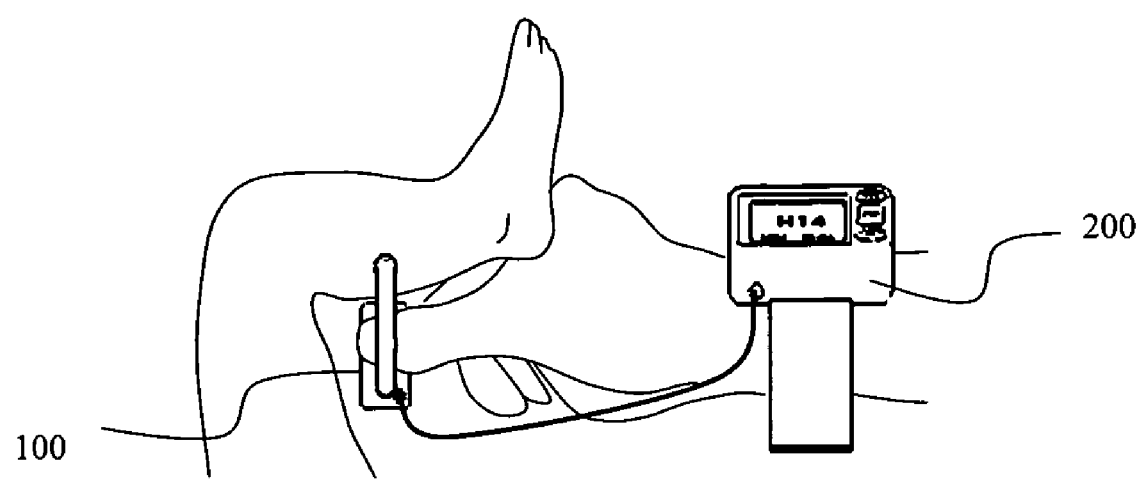
FIG. 2—General view of the infant hydration monitor in use.

FIG. 2 shows the general concept of the infant hydration monitor comprising a probe 100 connected to the electronic unit 200 equipped with a display. It is a compact, ergonomic, light-weight (preferably less than 100 g), low-power consumption battery-fed device that requires only a few seconds to take measurements. An operator wears the electronic unit 200 via Velcro straps or other wrist-mount strap means and with two fingers placed into the first and second finger openings 111 and 121, adjusts the distance between transducers 112 and 122 so as to position them appropriately about the infant's calf. The contact tips of the probe are optionally covered by disposable thin covers 113.

The infant hydration monitor includes a hand-held probe 100 and a compact electronic unit 200 with an integrated display, the unit 200 may optionally be connected wirelessly to a computer. The working frequency of the probe is selected to be generally about 5-15 MHz and preferably about 8-10 MHz. This higher frequency will help achieve the required accuracy of ultrasound pulse time-of-flight measurements (about 25 ns).

Another reason for choosing a higher frequency is related to the need for making a miniature probe with smaller transducers. To have the necessary directivity of ultrasonic wave, the ratio of the transducers' diameter to ultrasonic wavelength is selected to be in the range of about 20-50. At 10 MHz frequency, the sound wavelength in tissue is about 0.15 mm and respectively, transducers with the diameter in the range of 3-5 mm are used, which is quite adequate for the compact infant hydration monitor probe.

Figure 3:
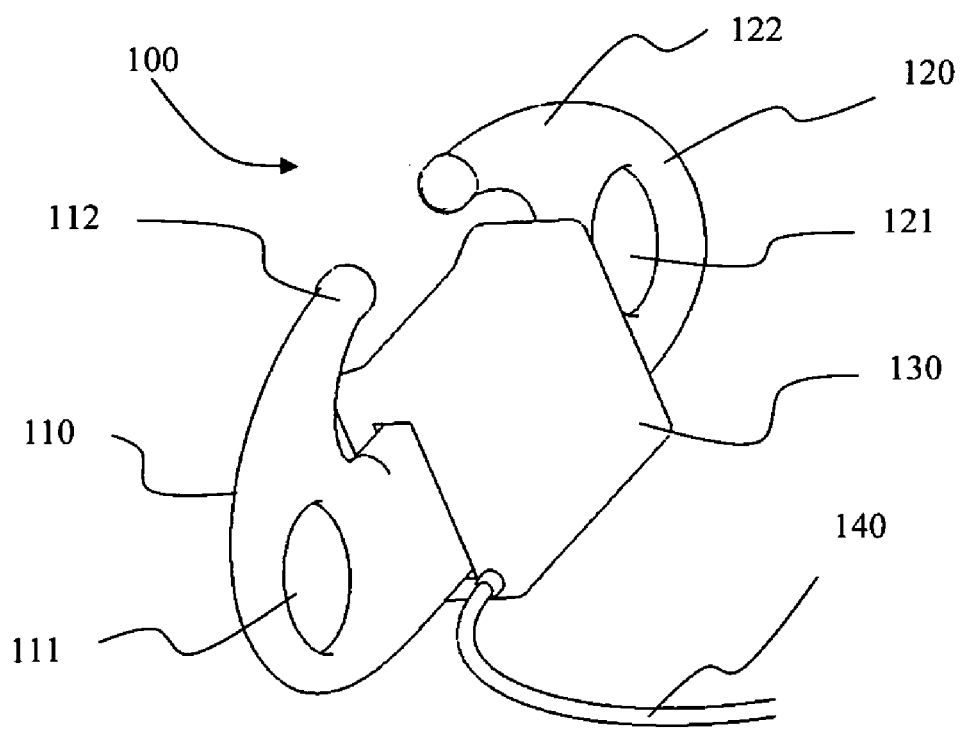
FIG. 3—General isometric view of the probe of the invention.

FIG. 3 shows the general design of the probe 100 and its components. A base of the probe housing 130 includes inside a sliding distance measuring means allowing the arms 110 and 120 to slide relative to each other. Any known high precision sliding means can be used such as for example a rack-and-pinion or other gear-based mechanisms or using a disk encoder to translate sliding motion into a digital position signal. The art of such mechanisms is well known from digital calipers and can be directly applied here. Exemplary designs include those described in the U.S. Pat. Nos. 6,687,646; 6,279,248; and 5,973,494 incorporated herein in their entirety by reference. In a typical digital caliper, a resolution of about 10 micrometer can be achieved, which is sufficient enough for the purpose of this device. The accuracy of the device should be within about 25 micrometers which makes it possible to use existing digital calipers as a base of the probe. In the preferred embodiment of the device, one arm is fixed to the housing 130 while another can slide in and out. The distance between the ends of the arms 112 and 122 is measured at all times and is transmitted to the electronic unit 200 for further calculations of the ultrasound velocity as described below.

Figure 4:
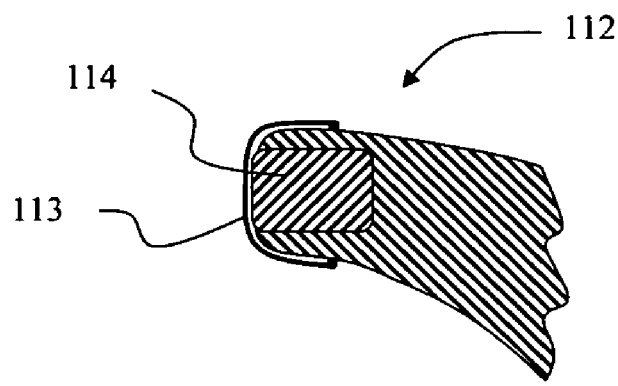
FIG. 4—Cross-sectional view a transducer arm of the probe.
Figure 5:
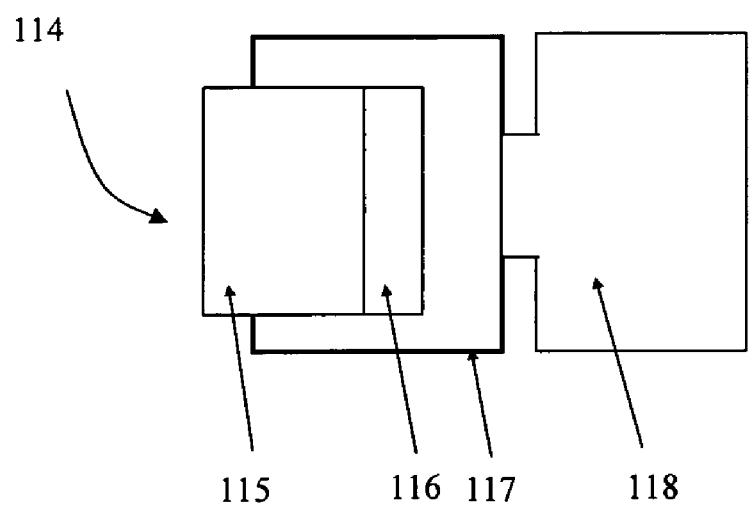
FIG. 5—Schematic block-diagram of the components of the transducer arm of the probe equipped with a force meter.

The probe 100 also includes ultrasonic transducers mounted on movable relative to each other arms 110 and 120 of the probe. Each end of the probe arms 112 and 122 include a broadband ultrasound transducer 114 as shown on FIG. 4, which is optionally covered by a disposable cover 113. One transducer is used as a transmitter while another one is used as a receiver. One of the arms of the probe includes several functional components as illustrated schematically on FIG. 5. Starting from the most external side of the arm, it includes an ultrasonic wave guide 115 located on a piezoceramic disk 116 and mounted within a transducer enclosure 117. This assembly in turn is mounted on a force meter 118 designed to provide contact pressure information between the sensors of the device and the skin of the infant. Only one of the two transducers is equipped with a force meter. This drawing illustrates the transducer 114 as having such sensor.

The broadband ultrasonic transmitter and the receiver transducers are preferably made of piezoceramic PZT disks that are axially aligned. The working stroke of the device is selected to be about 10-30 mm. The probe is manipulated by operator's fingers (thumb and forefinger) inserted in the openings 111 and 121 of the probe 100. Design for the piezoceramic transducer for accurate measurement of ultrasound velocity in tissue is similar to that described in the parent application.

An important feature of the device is controlled pressure exerted by the transducers on the tissue. The pressure should be within certain limits: sufficiently high to provide a reliable acoustical contact between the transducers and the tissue and at the same time below the level, which may cause any discomfort to the infant or unnecessary pressure on the skin. For reliable contact, just a few grams of force are required, which is well within the safety margin for neonatal skin. An optional two-color light diode may be mounted on the probe housing 130 so as to provide pressure information to the operator (not shown on the drawings). The diode has 3 states: no light—when the probe is disengaged, green—when the pressure is within the necessary for the measurement limits, and red—when the pressure is getting close to the allowed upper limit. At the beginning of examination, the operator gently moves the arms of the probe pressing the tested tissue between the transducers and stops the motion when the green light appears. In case when the operator sees red light, he/she slightly releases the probe to get back to the green light region. The device is optionally limited to take measurement only in the range of skin contact pressures corresponding to the green light.

Another improvement of the present invention is the use of an optional temperature probe to measure the skin temperature of the calf region as it is being measured. To accomplish this, an optional thermistor or another temperature sensor is mounted on one of the arms next to a transducer (not shown) so as to be in contact with the skin of the infant. The temperature value will be used by the processor to obtain a corrected level of hydration based on known temperature slope of ultrasound velocity. All data from the probe is communicated to the electronic unit wirelessly or via a cord 140.

Figure 6:
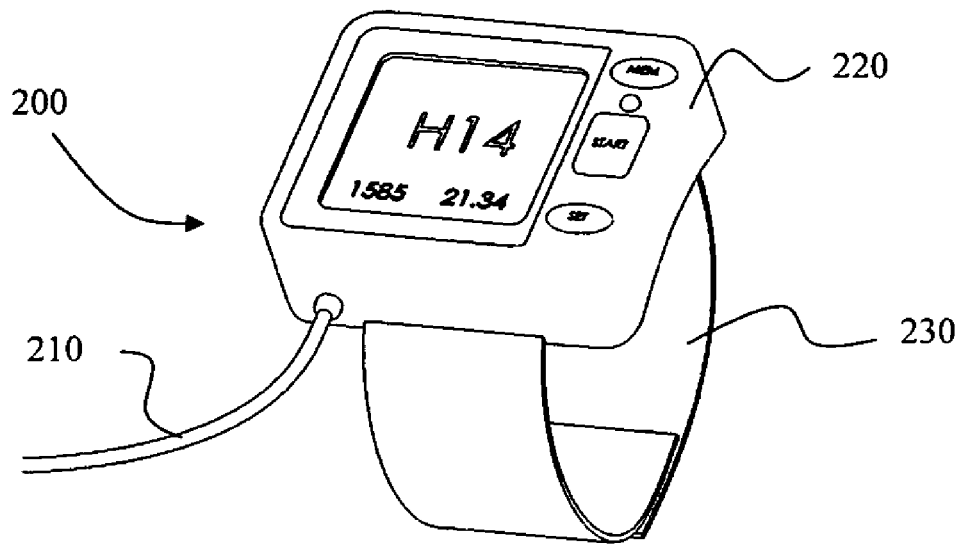
FIG. 6—General isometric view of a preferred configuration of the electronic unit with a display.
Figure 7:
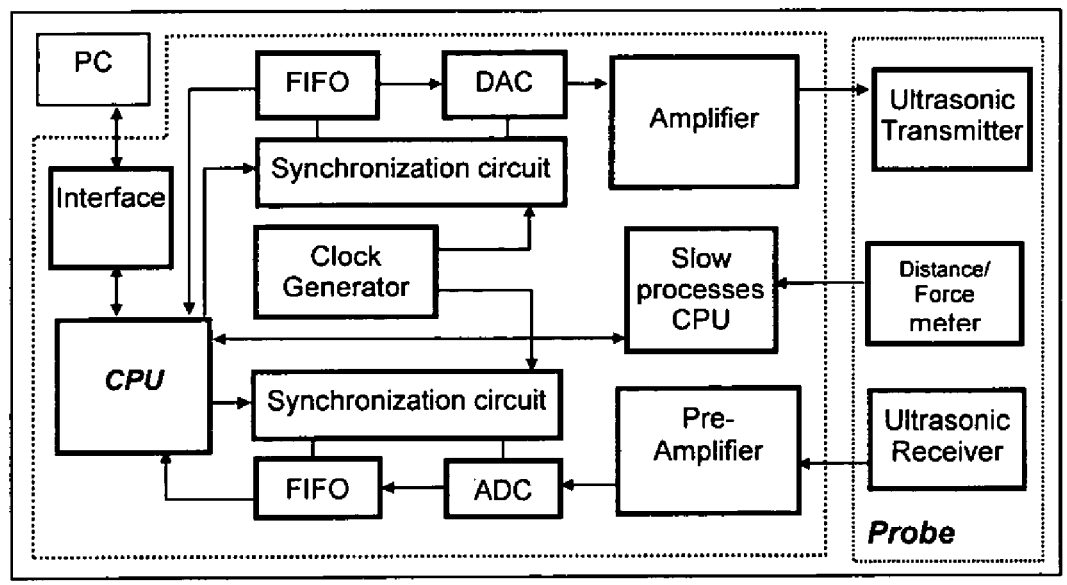
FIG. 7—Schematic block-diagram of the electronic unit.

The electronic unit 200 is based on the general block-diagram of the parent application. FIG. 7 shows a block-diagram of one preferred design optimized for the infant hydration monitor system. The CPU of the measurement circuit is preferably a CY62013 processor of Cypress Semi-conductor with embedded ADC, which manages ultrasonic measurements, acoustic base measurements and pressing force controls. 9-bit ADC and DAC of Analogue Device may be employed to obtain the necessary dynamic range. Excitation waveform (a short tone burst) may be downloaded from microprocessor memory. Series of multiple repeated received ultrasonic signals are recorded in FIFO memory and sent to the processor for processing. FIFO memory elements may provide 1 MbB/s data transfer speed to the processor, which is sufficient to provide real-time feedback for data acquisition control. Excitation peak-to-peak voltage for the ultrasonic emitter may preferably be in the range of 10-40V. The electronic unit 200 includes a display to indicate the results of the measurements to the user. It may also include an optional wireless interface to connect to the outside PC. In the most compact version of the device as generally shown on FIG. 6, the data transmission cord 210 is attached to the electronic unit 220, which in turn is adapted to be wrist-mounted via a strap 230 such as Velcro or other similar strap means.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An infant hydration monitor comprising:
    a hand-held probe including a probe housing equipped with a sliding distance measuring means, a first arm, a second arm, either said first arm or said second arm slidingly extending from said sliding distance measuring means, said first arm having a first end extending therefrom and equipped with a broadband ultrasonic transmitter, said second arm having a second end extending therefrom and equipped with a broadband ultrasonic receiver, said first and second ends operably located opposite each other and adapted to be placed against tissue of the infant, and
    an electronic unit having a display and adapted to receive ultrasound data and distance measuring data from said probe and calculate tissue hydration from said ultrasound and distance measuring data.

2. The monitor as in claim 1, wherein said electronic display unit is equipped with a wrist strap means and shaped to be worn on a wrist of a user.

3. The monitor as in claim 1, wherein said electronic unit adapted to calculate velocity of ultrasound through said tissue from said ultrasound and distance measuring data, said electronic means further adapted to indicate an increase of about 1 percent in tissue hydration for every decrease of about 3 to 4 meters per second of said velocity, said electronic unit also adapted to indicate a decrease of about 1 percent in tissue hydration for every increase of about 3 to 4 meters per second of said velocity.

* * * * *